United States Patent [19]
Wagner et al.

[11] Patent Number: 6,124,242
[45] Date of Patent: Sep. 26, 2000

[54] HERBICIDAL COMPOSITIONS AND PROCESSES BASED ON FERRODOXIN:NADP REDUCTASE INHIBITORS

[75] Inventors: Oliver Wagner, Ludwigshafen; Franz Röhl, Schifferstadt; Klaus Grossmann, Neuhofen; Ralf-Michael Schmidt, Kirrweiler; Uwe Sonnewald, Quedlinburg; Mohammad Hajirezaei, Gatersleben, all of Germany

[73] Assignee: BASF Aktiengesellschaft, Ludwigshafen, Germany

[21] Appl. No.: 09/336,731

[22] Filed: Jun. 21, 1999

[30] Foreign Application Priority Data

Jun. 26, 1998 [DE] Germany ............. 198 28 509

[51] Int. Cl.[7] ............. A01N 43/78; C07D 277/82
[52] U.S. Cl. ................. 504/170; 548/161
[58] Field of Search .............. 548/161; 504/170

[56] References Cited

U.S. PATENT DOCUMENTS

| | | | |
|---|---|---|---|
| 3,245,787 | 4/1966 | Williams | 430/361 |
| 3,525,614 | 8/1970 | Jacken | 430/361 |
| 3,634,013 | 1/1972 | Maul et al. | 8/409 |
| 3,721,823 | 3/1973 | Van Lishout et al. | 430/365 |
| 3,933,493 | 1/1976 | Ohyama et al. | 430/214 |
| 4,252,959 | 2/1981 | Spitzner | 546/306 |
| 5,554,196 | 9/1996 | Wielstra | 8/444 |
| 5,563,031 | 10/1996 | Yu | 435/4 |
| 5,719,034 | 2/1998 | Kiser et al. | 435/14 |

FOREIGN PATENT DOCUMENTS

| | | |
|---|---|---|
| 704027 | 9/1967 | Belgium . |
| 704027 | 3/1968 | Belgium . |
| 2046393 | 8/1992 | Canada . |
| 465901 | 1/1992 | European Pat. Off. . |
| 628424 | 12/1994 | European Pat. Off. . |
| 1942661 | 8/1969 | Germany . |
| 1942661 | 2/1970 | Germany . |
| 2105063 | 8/1972 | Germany . |
| 2232523 | 5/1973 | Germany . |
| 4420093 | 9/1995 | Germany . |
| 63-85628 | 4/1988 | Japan . |
| 975932 | 11/1964 | United Kingdom . |
| 2056103 | 3/1981 | United Kingdom . |
| 95/23967 | 9/1995 | WIPO . |
| 96/07757 | 3/1996 | WIPO . |

OTHER PUBLICATIONS

Shin et al., *J. Biol. Chem.*, 240,1965, pp. 1405–1411.
Bowsher et al., *The Plant Journal*, 1993, 3(3), 463–467.
Gillham et al., *Proc. Br., Crop. Prot. Conf.—Weeds*, 1985, pp. 1195–1201.
Hofgen et al., *Plant Physiol.*, 1995, 107, 469–477.
Hünig et al., *Justus Liebigs Ann. der Chem.*, 679, 1966, 116–139.
Hünig et al., *Justus Liebigs Ann. der Chem.*, 700, 1966, 65–77.
*Chem. Abst.* 54:17372c, 1960.

*Primary Examiner*—Fiona T. Powers
*Attorney, Agent, or Firm*—Keil & Weinkauf

[57] ABSTRACT

There are described ferredoxin:NADP reductase inhibitors, an assay system for the search for such inhibitors, and their use as herbicides.

3 Claims, 2 Drawing Sheets

Figure 1: Nucleotide and protein sequences of the complete FNR clone

Nucleotide sequence:

| | |
|---|---|
| 1    | TTTCTCTGTA TCATAAACAT GGCTACTGCA GTAAGTGCTG CAGTTTCTCT |
| 51   | TCCTTCATCC AAGTCCACCT CTTTTTCCTC TAGAACCTCC ATCATCTCCA |
| 101  | CTGACAAAAT CAACTTCAAC AAGGTGCCTT TGTACTACAG AAATGTGTCA |
| 151  | GGTGGTAGTA GATTAGTTTC TATCAGAGCC CAAGTGACCA CTGAGGCTCC |
| 201  | TGCTAAAGTG GAGAAGATTT CAAAGAAACA GGATGAAGGT GTGATTGTGA |
| 251  | ATAAATTCAG GCCAAAGGAA CCTTATGTTG GTAGATGTCT ACTAAACACT |
| 301  | AAGATCACTG GTGATGATGC ACCTGGTGAA ACTTGGCACA TGGTTTTTAG |
| 351  | CACTGAGGGA GAGGTCCCAT ATAGAGAAGG ACAATCCATT GGTGTGATTG |
| 401  | CTGATGGTGT TGATGCCAAT GGGAAGCCTC ACAAGCTTAG ATTGTACTCA |
| 451  | ACTGCTAGCA GTGCCCTTGG TGACTTCGGT GACTCCAAAA CCGTTTCCCT |
| 501  | GTGTGTCAAG AGGCTTGTGT ACACCAATGA CAAAGGGGAA GAAGTTAAAG |
| 551  | GAGTTTGCTC AAACTTCTTA TGTGACTTGA AGCCTGGAGC AGAGGTCAAG |
| 601  | ATTACTGGAC CTGTAGGCAA AGAAATGCTC ATGCCTAAAG ATCCAAATGC |
| 651  | CACCGTTATA ATGCTTGCCA CTGGAACTGG AATTGCTCCT TTCCGTTCAT |
| 701  | TCCTGTGGAA AATGTTCTTT GAGAAACACG AGGACTACAA GTTCAACGGT |
| 751  | ACCGCATGGC TTTTCTTGGG TGTTCCCACC AGCAGCTCAC TACTTTACAA |
| 801  | GGAGGAATTC GAGAAAATGA AGGAGAAGGC CCCGGAAAAC TTCAGATTGG |
| 851  | ACTTTGCTGT GAGCAGAGAG CAAACGAACG AAAAGGGTGA AAGATGTAC |
| 901  | ATTCAAACCA GAATGGCTCA ATATGCTGAA GAACTATGGA CTTTGCTCCA |
| 951  | AAAAGACAAC ACCTTCATCT ACATGTGTGG ACTCAAGGGC ATGGAGCAGG |
| 1001 | GAATTGATGA AATTATGTCT GCTCTTGCTG AAAGAGATGG TATTGTCTGG |
| 1051 | GCGGACTACA AGAAGCAATT GAAGAAGGCA GAGCAATGGA ATGTTGAAGT |
| 1101 | CTACTAAATA TTTTTACTTT TCTTTGTACA AATATGAGCC AACTTTATGC |
| 1151 | TTCTCTCCCC CTGCATCCAT GTAGATAGGT AAATTTTTCC TTTGAAATTT |
| 1201 | TAATTTCATT TTTTGGGACT TCCCTTTTTA AATCTTTCAT CTGTATCTTT |
| 1251 | TAATGAATCA GTATATTCGG CGGCCGCGAA TTCCTGCAGC CCGGGGGATC |
| 1301 | CACTAGTTCT AGAGCGGCCG CCACCGCGGT GGA |

Protein sequence:

| | |
|---|---|
| 1   | MATAVSAAVS LPSSKSTSFS SRTSIISTDK INFNKVPLYY RNVSGGSRLV |
| 51  | SIRAQVTTEA PAKVEKISKK QDEGVIVNKF RPKEPYVGRC LLNTKITGDD |
| 101 | APGETWHMVF STEGEVPYRE GQSIGVIADG VDANGKPHKL RLYSTASSAL |
| 151 | GDFGDSKTVS LCVKRLVYTN DKGEEVKGVC SNFLCDLKPG AEVKITGPVG |
| 201 | KEMLMPKDPN ATVIMLATGT GIAPFRSFLW KMFFEKHEDY KFNGTAWLFL |
| 251 | GVPTSSSLLY KEEFEKMKEK APENFRLDFA VSREQTNEKG EKMYIQTRMA |
| 301 | QYAEELWTLL QKDNTFIYMC GLKGMEQGID EIMSALAERD GIVWADYKKQ |
| 351 | LKKAEQWNVE VY |

Figure 2

HERBICIDAL COMPOSITIONS AND PROCESSES BASED ON FERRODOXIN:NADP REDUCTASE INHIBITORS

The present invention relates to ferredoxin:NADP reductase inhibitors, a test system for searching for such inhibitors, and their use as herbicides.

Ferredoxin:NADP reductase (EC 1.18.1.2; FNR) is an enzyme which is involved in the provision of reduction equivalents for the assimilation of carbon, nitrogen and sulfur in plants. The enzyme catalyzes the following reaction:

reduced ferredoxin+NADP⇌oxidized ferredoxin+NADPH

During photosynthesis, the reaction proceeds with formation of NADPH (Shin, M. and Arnold, D. I., J. Biol. Chem. 240(1965), 1405–1411), while reduced ferredoxin is formed in non-photosynthetic tissue (Bowsher, C. G. et al., Plant J. 3(1993), 463–467).

It is known that photosynthesis inhibitors are suitable for use as herbicides. These herbicides act as photosystem II inhibitors, like, for example, atrazin (Hock, B., Fedtke, C. and Schmidt, R. R. (1995) Herbizide, Georg Thieme Verlag) or as redox catalysts on photosystem I, like, for example, paraquat (Hock, B., Fedtke, C. and Schmidt, R. R. (1995) Herbizide, Georg Thieme Verlag).

It has been reported that the herbicide oxyfluorfen, when exposed to light, has an effect on ferredoxin:NADP reductase (Gillham et al., (1985) Proc. Br. Crop Prot. Conf.—Weeds, 1195–1201). However, in view of the known effect of oxyfluorfen on protoporphyrinogen IX oxidase (Hock, B., Fedtke, C. and Schmidt, R. R. (1995) Herbizide, Georg Thieme Verlag) and the related light-dependent formation of reactive oxygen, this action can be attributed to indirect effects and is therefore irrelevant for the herbicidal action.

Ferredoxin:NADP reductase inhibitors as herbicides were hitherto unknown. It can be assumed that inhibition of the provision of reduction equivalents for assimilation greatly affects the growth of plants.

It is an object of the present invention to provide inhibitors of the enzyme ferredoxin:NADP reductase and to find their use as herbicides.

We have found that this object is achieved by ferredoxin:NADP reductase inhibitors of the formula I, where =⌇NH— represents the E/Z isomers, which have been found for the first time by using a ferredoxin:NADP reductase test.

Formula I

$R^1$, $R^2$, $R^3$: in each case independently of one another are hydrogen, halogen, cyano, $C_1$–$C_6$-alkyl, $C_1$–$C_6$-alkoxy, $C_1$–$C_6$-alkoxyalkyl, $C_1$–$C_6$-haloalkyl, $C_1$–$C_6$-alkylthio, $C_1$–$C_6$-haloalkoxy, $C_1$–$C_6$-alkylcarbonyl, $C_1$–$C_6$-alkoxycarbonyl, $S(O)_n$-$C_1$–$C_6$-alkyl, $S(O)_n$-$C_1$–$C_6$-haloalkyl, $S(O)_n$—N-$C_1$–$C_6$-alkyl, $S(O)_n$—N($C_1$–$C_6$-alkyl)$_2$ where n=0, 1, 2, $SO_3H$, COOH, $PO_3H$, $CONH_2$, CONH-$C_1$–$C_6$-alkyl, CO—N($C_1$–$C_6$-alkyl)$_2$, $NH_2$, NH-$C_1$–$C_6$-alkyl, N-($C_1$–$C_6$-alkyl)$_2$, $R^4$: hydrogen, $C_1$–$C_6$-alkyl,

Y: CO, $SO_2$ $R^5$,$R^6$,$R^7$: hydrogen, halogen, cyano, $C_1$–$C_{30}$-alkyl, $C_1$–$C_{30}$-alkoxyalkyl, $C_1$–$C_{30}$-haloalkyl, $C_1$–$C_{30}$-alkylthio, $C_1$–$C_{30}$-haloalkoxy, $C_1$–$C_{30}$-alkylcarbonyl, $C_1$–$C_{30}$-alkoxycarbonyl, $SO_3H$, $S(O)_n$-$C_1$–$C_{30}$-alkyl, $S(O)_n$-$C_1$–$C_{30}$-haloalkyl, $S(O)_n$—N-$C_1$–$C_{30}$-alkyl, $S(O)_n$—N($C_1$–$C_{30}$-alkyl)$_2$ where n=0, 1, 2, COOH, $CONH_2$, CONH-$C_1$–$C_{30}$-alkyl, CO—N($C_1$–$C_{30}$-alkyl)$_2$, $NH_2$, NH-$C_1$–$C_{30}$-alkyl, N-($C_1$–$C_{30}$-alkyl)$_2$ Some of the compounds of the formula I are known from the literature or can be prepared analogously (for example GB 975932, BE 704027, BE 665033, DE 1942661, Lieb. Ann. Chem. 700 (1966) 65).

a)

b)

where Y=CO or $SO_2$ and $R^5$, $R^6$, $R^7$ independently of one another may be the following radicals: hydrogen, halogen, cyano, $C_1$–$C_{30}$-alkyl, $C_1$–$C_{30}$-alkoxyalkyl, $C_1$–$C_{30}$-haloalkyl, $C_1$–$C_{30}$-alkylthio, $C_1$–$C_{30}$-haloalkoxy, $C_1$–$C_{30}$-alkylcarbonyl, $C_1$–$C_{30}$-alkoxycarbonyl, $SO_3H$, $S(O)_n$-$C_1$–$C_{30}$-alkyl, $S(O)_n$-$C_1$–$C_{30}$-haloalkyl, $S(O)_n$—N-$C_1$–$C_{30}$-alkyl, $S(O)_n$—N($C_1$–$C_{30}$-alkyl)$_2$ where n=0, 1, 2, COOH, $CONH_2$, CONH-$C_1$–$C_{30}$-alkyl, CO—N($C_1$–$C_{30}$-alkyl)$_2$, $NH_2$, NH-$C_1$–$C_{30}$-alkyl, N-($C_1$–$C_{30}$-alkyl)$_2$.

Alternatively, compounds of the formula I can be prepared as described in BE 704027 or Lieb. Ann. Chem. 623 (1959), 191.

a)

-continued b)

Table A contains compounds of the formula I A, each line corresponding to one compound of the formula I A.

TABLE A

Formula IA

| | $R^1$ | $R^4$ | $R^5$ |
|---|---|---|---|
| A.1 | H | Et | 4-$NH_2$ |
| A.2 | H | Me | 2,5-di-Cl |
| A.3 | H | Me | 4-COOH |
| A.4 | H | Me | 3-$SO_3H$ |
| A.5 | H | Me | 4-Me |
| A.6 | H | Me | H |
| A.7 | H | Me | 4-Me |
| A.8 | H | Me | 3-$NO_2$ |
| A.9 | H | Me | H |
| A.10 | H | Me | 3-O—$(CH_2)_{11}$Me |
| A.11 | 6-MeO | Me | H |
| A.12 | H | Me | 2,4-di-C(Me)$_2C_2H_5$ |
| A.13 | H | Et | H |
| A.14 | H | Me | 2-O—$(CH_2)_{15}$Me-5-COOH |
| A.15 | 5-F2CHSO2 | Me | 3-COOH-4-$SO_2$—$(CH_2)_{15}$Me |
| A.16 | 5-SO3H | Me | 3-COOH-4-$SO_2$—$(CH_2)_{15}$Me |
| A.17 | H | Me | 3-COOH-4-O—$(CH_2)_{15}$Me |
| A.18 | H | Me | 2-O—$(CH_2)_{15}$Me-5-COOH |
| A.19 | 6-SO3H | Me | 3-COOH-4-O—$(CH_2)_{15}$Me |
| A.20 | 5-SO3H | Me | 3-COOH-4-O—$(CH_2)_{15}$Me |
| A.21 | 5-SO2CHF2 | Me | 3-COOH-4-O—$(CH_2)15$Me |
| A.22 | 6-F | Me | 2-O—$(CH_2)_{15}$Me-5-COOH |
| A.23 | 6-Cl | Me | 2-O—$(CH_2)_{15}$Me-5-COOH |
| A.24 | 4,6-di-Cl | Me | 2-O—$(CH_2)_{15}$Me-5-COOH |
| A.25 | 5-$CF_3$ | Me | 2-O—$(CH_2)_{15}$Me-5-COOH |
| A.26 | 5-Cl | Me | 2-O—$(CH_2)_{15}$Me-5-COOH |
| A.27 | H | Me | 2-O—$(CH_2)_{15}$Me-5-COOEt |
| A.28 | 5-$SO_3H$ | Me | 2-O—$(CH_2)_{15}$Me-5-COOH |
| A.29 | H | Me | 4-COOEt |
| A.30 | H | Me | 4-OMe |
| A.31 | H | Me | 4-Ci |
| A.32 | H | Me | 2-$NO_2$ |
| A.33 | H | Et | 3-$NH_2$ |
| A.34 | 5-$SO_2CHF_2$ | Me | 3-COOH-4-$SO_2$—$(CH_2)_{15}$Me |
| A.35 | 5-$SO_3H$ | Me | 3-COOH-4-$SO_2$—$(CH_2)_{15}$Me |
| A.36 | H | Me | 4-$NO_2$ |
| A.37 | H | Et | 3-NH—CO—$C_9H_{19}$ |
| A.38 | 6-$SO_2NH_2$ | Me | 3-COOH-4-O—$(CH_2)_{15}$Me |
| A.39 | H | Et | 3-$NH_2$ |
| A.40 | H | CH=CH | 4-NHCOMe |
| A.41 | H | Me | 3-COOH-4-OH |
| A.42 | H | Et | 4-$NO_2$ |
| A.43 | H | Me | 4-$SO_2F$ |
| A.44 | H | Me | 4-$SO_3H$ |
| A.45 | 6-O-Me | Me | 3-COOH-4-OH |
| A.46 | 6-$SO_3H$ | Me | 3-NHCOMe-4-$SO_2$—$C_{16}H_{33}$ |
| A.47 | 5-$SO_2CF_2$ | Me | 3-$NHSO_2$—$C_{16}H_{33}$ |
| A.48 | 5-$SO_3H$ | Me | 3-$NMeSO_2$—$C_{16}H_{33}$ |
| A.49 | 5-$SO_3H$ | Me | 3-COOH-4-$SO_2$—$C_{16}H_{33}$ |
| A.50 | H | Me | 4-O—$C_{16}H_{33}$ |
| A.51 | H | Me | 4-$SO_2$—NH—$C_{16}H_{33}$ |
| A.52 | 5-$SO_3H$ | Me | 4-$SO_2$—NH—$C_{16}H_{33}$ |
| A.53 | H | Me | 4-$SO_2$—NMe—$C_{16}H_{33}$ |

TABLE A-continued

Formula IA

| | $R^1$ | $R^4$ | $R^5$ |
|---|---|---|---|
| A.54 | $C_{15}H_{31}$ | Me | 3-COOH |
| A.55 | 5-$SO_2CF_2H$ | Me | 4-$SO_2$—NH—$C_{16}H_{33}$ |
| A.56 | 5-$SO_2CF_2H$ | Me | 3-CO—NH—$C(C_4H_9)_3$ |
| A.57 | H | Me | 4-CO—NHMe |
| A.58 | 5-$SO_2CF_2H$ | Me | 4-$SO_2$—NH—$C(C_4H_9)_3$ |
| A.59 | 4,6-di-Ci | Me | 2-O—$C_{16}H_{33}$-5-COOH |

Table B contains compounds of the formula I B, each line corresponding to one compound of the formula I B.

TABLE B

Formula IB

| | $R^1$ | $R^4$ | $R^5$ | $R^6$ |
|---|---|---|---|---|
| B.1 | H | Et | H | H |
| B.2 | H | Me | H | H |
| B.3 | 5-$SO_3H$ | CH3 | 3-$SO_3H$ | 6-$SO_2$—$C_{16}H_{33}$ |

Table C contains compounds of the formula I C, each line corresponding to one compound of the formula I C.

TABLE C

Formula IC

| | $R^1$ | $R^4$ | $R^5$ |
|---|---|---|---|
| C.1 | H | Me | 2-OH |

The effect of herbicides can be simulated by generating transgenic plants. Such plants contain the antisense information of a gene, which leads to repression of the gene and thus corresponds to an enzyme inhibition situation, as has been shown, by way of example, on acetolactate synthase (Hofgen et al., Plant Physiol. 107(1995), 469–477).

Examples 1–3 given further below describe the generation of a transgenic tobacco plant which expresses the antisense construct to the ferredoxin:NADP reductase gene.

FIG. 1 shows the nucleotide and protein sequences of the complete FNR clone.

Accordingly, transgenic plants were generated which exhibit reduced expression of ferredoxin:NADP reductase.

In fact, reduced growth and a reduced FNR enzyme activity can be observed in these plants, as can be seen from Example 4.

The present invention furthermore relates to the use of a test system for identifying ferredoxin:NADP reductase inhibitors with potentially herbicidal action, and to methods for identifying substances which have a potentially herbicidal or growth-regulatory action caused by inhibition or inactivation of a plant ferredoxin:NADP reductase, which involves a) first generating, in a transgenic organism or transgenic cell, the enzyme ferredoxin:NADP reductase by heterologous expression of a DNA sequence encoding this transport protein, then b) employing this recombinant organism as a whole or a cell digest of this organism for investigating a chemical compound for its inhibitory action on the enzyme ferredoxin:NADP reductase, and c) testing the compound which is active against the enzyme zerredoxin:NADP reductase for its herbicidal or growth-regulatory activity on plants.

The recombinant organism employed may be a single-celled organism or a plant cell.

The enzyme ferredoxin:NADP reductase (ferredoxin:NADP oxidoreductase, E.C. 1.18.1.2) from spinach leaves—obtainable from Sigma, Germany—may be used for establishing the test system.

The invention furthermore relates to the use of the compounds of the formula I as herbicides or for the desiccation/defoliation of plants, herbicidal compositions and compositions for the desiccation/defoliation of plants which comprise the compounds of the formula I as active substances, processes for the preparation of the compounds of the formula I and herbicidal compositions and compositions for the desiccation/defoliation of plants using the compounds of the formula I, methods of controlling undesirable vegetation and for the desiccation/defoliation of plants using the compounds of the formula I.

There have furthermore been found herbicidal compositions which comprise the compounds of the formula I and which have a very good herbicidal action. Moreover, there have been found processes for the preparation of these compositions and methods of controlling undesirable vegetation using the compounds of the formula I.

In addition, it has been found that the compounds of the formula I are also suitable for the desiccation/defoliation of plant organs, suitable plants being crop plants such as cotton, potatoes, oilseed rape, sunflowers, soyabeans or field beans, in particular cotton. In this respect, there have been found compositions for the desiccation and/or defoliation of plants, processes for the preparation of these compositions, and methods for the desiccation and/or defoliation of plants using the compounds of the formula I.

Agriculturally useful salts are to be understood as meaning mainly the salts of I with those cations, and acid addition salts of I with those acids, which do not adversely affect the herbicidal or desiccant/defoliant action of I.

Thus, suitable cations are, in particular, the ions of the alkali metals, preferably sodium and potassium, of the alkaline earth metals, preferably calcium, magnesium and barium, and of the transition metals, preferably manganese, copper, zinc and iron, and also the ammonium ion which may have attached to it a $C_1$–$C_4$-alkyl, phenyl or benzyl substituent and, if desired, additionally one to three further $C_1$–$C_4$-alkyl radicals, preferably diisopropylammonium, tetramethylammonium, tetrabutylammonium, trimethylbenzylammonium, furthermore phosphonium ions, preferably tri-($C_1$–$C_4$-alkyl)-phosphonium, sulfonium ions, preferably tri-($C_1$–$C_4$-alkyl)-sulfonium, and sulfoxonium ions, preferably tri-($C_1$–$C_4$-alkyl)-sulfoxonium.

Agriculturally useful salts of the compounds of the formula I can be formed by reacting the cation in question with a base, preferably an alkali metal hydroxide or alkali metal hydride, or by reacting the anion in question with an acid, preferably hydrochloric acid, hydrobromic acid, sulfuric acid, phosphoric acid or nitric acid.

Salts of I whose metal ion is not an alkali metal ion can also be prepared in the customary manner by double decomposition of the corresponding alkali metal salt, also ammonium, phosphonium, sulfonium and sulfoxonium salts by means of ammonia, phosphonium hydroxide, sulfonium hydroxide or sulfoxonium hydroxide.

The compounds of the formula I and their agriculturally useful salts are suitable as herbicides, both in the form of isomer mixtures and in the form of the pure isomers. The herbicidal compositions comprising I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

Moreover, the compounds of the formula I can also be used in crops which tolerate the action of herbicides due to breeding including genetic engineering methods.

Furthermore, the substituted compounds of the formula I are also suitable for the desiccation and/or defoliation of plants.

As desiccants, they are especially suitable for desiccating the aerial parts of crop plants such as potatoes, oilseed rape, sunflowers and soybeans. This allows completely mechanical harvesting of these important crop plants.

Also of economic interest is facilitated harvesting, which is made possible by concentrating, over a period of time, dehiscence, or reduced adhesion to the tree, in the case of citrus fruit, olives or other species and varieties of pomaceous fruit, stone fruit and nuts. The same mechanism, i.e. promotion of the formation of abscission tissue between fruit or leaf and shoot of the plants is also essential for readily controllable defoliation of useful plants, in particular cotton.

Moreover, a shortened period of time within which the individual cotton plants ripen results in an increased fiber quality after harvesting.

The compounds I of the formula, or the compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dlspersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenvl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite with liquors or methylcellulose.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples below illustrate the preparation of such products:

I. 20 parts by weight of the compound of the formula I are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound of the formula I are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the compound of the formula I are mixed thoroughly with 3 parts by weight of sodium diisobutylnaphthalene-$\alpha$-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the compound of the formula I are mixed with 97 parts by weight of finely divided kaolin. This gives a dust which comprises 3% by weight of the active ingredient.

VI. 20 parts by weight of the compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound of the formula I is dissolved in a mixture composed of 70 parts by weight of cyclohexanone, 20 parts by weight of ethoxylated isooctylphenol and 10 parts by weight of ethoxylated castor oil. The mixture can subsequently be diluted with water to give the desired concentration of active ingredient. This gives a stable emulsion concentrate.

VIII. 1 part by weight of the compound of the formula I is dissolved in a mixture composed of 80 parts by weight of cyclohexanone and 20 parts by weight of Wettol® EM 31 (=non-ionic emulsifier based on ethoxylated castor oil; BASF AG). The mixture can subsequently be diluted with water to give the desired concentration of active ingredient. This gives a stable emulsion concentrate.

The compounds of the formula I, or the herbicidal compositions, can be applied pre- or post-emergence. If the active ingredients are less well tolerated by certain crop plants, application techniques may be used in which the herbicidal compositions are sprayed, with the aid of the sprayers, in such a way that they come into as little contact, if any, with the leaves of the sensitive crop plants while reaching the leaves of undesirable plants which grow underneath, or the bare soil (post-directed, lay-by).

Depending on the aim of the control measures, the season, the target plants and the growth stage, the application rates of compounds of the formula I are from 0.001 to 3.0, preferably 0.01 to 1.0 kg/ha active substance (a.s.).

To widen the spectrum of action and to achieve synergistic effects, the substituted compounds of the formula I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy-/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-$CF_3$-phenylderivatives, carbamates, quinolinecarboxytic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds of the formula I, alone or in combination with other herbicides, in the form of a mixture with additional other crop protection materials, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

EXAMPLE 1

Generation of a Transgenic Tobacco Plant which Expresses the Antisense Construct to the Ferredoxin:NADP Reductase Gene.

A. General Cloning Method

Cloning methods such as, for example: restriction cleavages, agarose gel electrophoresis, purification of DNA fragments, transfer of nucleic acids to nitrocellulose and nylon membranes, linkage of DNA fragments, transformation of E. coli cells, bacterial cultures, phage multiplication and sequence analysis of recombinant DNA were carried out as described by Sambrook et al. (1989) Cold Spring Harbor Laboratory Press (ISBN 0-87969-309-6). Agrobacterium tumefaciens was transformed following the method of Höfgen and Willmitzer (Nucl. Acid Res. 16 (1988), 9877). The agrobacteria were grown in YEB medium (Vervliet et al., J. Gen. Virol. 26 (1975), 33).

B. Generation of CDNA Libraries

To generate leaf-specific cDNA libraries, the total leaf RNA of untransformed tobacco plants (Sonnewald Plant J. 2 (1992), 571) was isolated by a method described by Logemann et al. (Anal. Biochem. 163 (1987), 21). The poly(A)-RNA was subsequently purified over oligo(dT)-cellulose type 7 (Pharmacia Biotech Europe, Munzgerstr. 9, 79111 Freiburg) following the manufacturer's instructions. After photometric determination of the concentration, 5 μg of the resulting RNA were used for cDNA synthesis. All chemicals and enzymes required for generating the cDNA were obtained from Stratagene (11099 North Torrey Pines Road, La Jolla, Calif. 92037, USA). The methods used were carried out following the manufacturer's instructions. The synthesis of the first and second cDNA strand was carried out using the λ-CAP-cDNA synthesis kit. The resulting double-strand cDNAs were subsequently provided with EcoRI-NotI adaptors and cloned into an EcoRI digested lambda ZAPII vector. After the recombinant lambda DNA had been packaged in vitro (Gigapack II packaging extract), XL-1 E. coli cells (Stratagene) were transformed. The titer of the cDNA libraries was determined by counting the plaques formed.

C. Generation of Polyclonal Antibodies Directed Against Membrane-bound Proteins

Membrane-bound proteins were isolated from approx. 400 g leaf material from tobacco plants (Nicotiana tabacum L. cv. Samsun NN) by means of differential centrifugation following standard processes. To obtain antisera, 100 μg of protein were used for immunizing mice.

D. Isolation of cDNA Clones Encoding Membrane-bound Proteins

To isolate cDNA clones which encode membrane-bound tobacco proteins, a leaf-specific cDNA library in λ-ZAPII (Stratagene) was screened with the aid of the antisera prepared. The cDNA library was plated out at a titer of $3\times10^5$ plaque-forming units. From these plates, plaques were transferred to nitrocellulose filters which had previously been soaked for 15 minutes in 10 mM IPTG. To detect phage carrying cDNa clones encoding membrane-bound proteins, the nitrocellulose filters were incubated with the specific antibodies (see C). Binding of the specific antibodies was subsequently detected by an enzyme-coupled second antibody and subsequent color reaction (Amersham-Buchler). These were subsequently picked out and subjected to a second screening to obtain uniform populations. 4 clones were purified down to individual plaques and sequenced. Clone OR15, which has a length of 1050 base pairs, encodes a 291 amino acid long polypeptide. The comparison of homology revealed that this polypeptide exhibits 80% identity to the bean FNR.

E. Isolation of a Complete FNR Clone

Since clone OR15 does not carry the entire FNR encoding region, a leaf-specific cDNA library in λ-ZAPII (Stratagene) was plated out at a titer of $3\times10^5$ plaque-forming units in order to isolate a complete FNR clone. From these plates plaques were transferred to nylon membrane and hybridized with the radiolabeled cDNA fragments used as probe (OR15). Due to hybridization of the probe with homologous cDNa fragments on the plaque filters, dark spots appear on the X-ray film caused by the radioactivity. Using these X-ray films, it is possible to identify the phages which carry the desired cDNA fragments. The isolated phages are stored in SM medium. 4 clones were obtained and characterized by restriction analysis. Since they only differ slightly with regard to sequence length, the sequence of the longest clone is given under F.

F. Sequencing the Plasmid DNA

The cDNA clones obtained in pBluescript were sequenced using specific primers. The binding sites of these primers in pBluescript are chosen in such a way that they allow sequencing reactions from the 5'-end and from the 3'-end of the cDNa clones. Nucleotide sequence (published in Jamsen, T. et al. Current Genetics 13(1988), 517–522) and protein sequence (published in Karplus, P. A. et al. Biochemistry 23(1984), 6576–6583) of the identified FNR are shown hereinbelow. The complete FNR clone is 1333 base pairs in length and carries an open reading frame encoding a 362 amino acid long polypeptide (FIG. 1).

C. Bacterial Strains

E. coli (XL-1 Blue) bacteria were obtained from Stratagene. The Agrobacterium tumefaciens strain employed for plant transformation (C58C1 carrying plasmid pGV 3850kan) was described by Debleare et al., Nucl. Acid Res. 13(1985), 4777.

H. Tobacco Transformation

To transform tobacco plants (*Nicotiana tabacum* L. cv. Samsun NN), 10 ml of an overnight culture of *Agrobacterium tumefaciens* which had been grown under selective conditions was centrifuged off, the supernatant was discarded, and the bacteria were resuspended in an equal volume of antibiotic-free medium. Leaf disks from sterile plants (diameter approx. 1 cm) were immersed in this bacterial solution in a sterile Petri dish. The leaf disks were subsequently plated in Petri dishes on MS medium (Murashige and Skoog, Physiol. Plant. 15 (1962), 473) supplemented with 2% sucrose and 0.8% Bacto agar. After incubation in the dark for 2 days at 25° C., they were transferred onto MS medium supplemented with 100 mg/l kanamycin, 500 mg/l claforan, 1 mg/l benzylaminopurin (BAP), 0.2 mg/l naphthylacetic acid (NAA), 1.6% glucose and 0.8% Bacto agar and cultivation was continued (16 hours light/8 hours dark). Growing shoots were transferred to hormone-free MS medium supplemented with 2% sucrose, 250 mg/l claforan and 0.8% Bacto agar.

I. Analysis of Total RNA from Plant Tissue

Total RNA from plant tissue was isolated as described by Logemann et al. (Anal. Biochem. 163 (1987), 21). For analysis, batches of 20–40 μg of RNA were separated in a formaldehyde-containing 1.5% strength agarose gel. After separation of the RNA molecules by electrophoresis, the RNA was transferred to a nylon membrane by means of capillary transfer. Specific transcripts were detected as described by Amasino (Anal. Biochem. 152 (1986), 304). The cDNa fragments used as probe were radiolabeled using a Random Primed DNA Labeling Kit (Boehringer, Mannheim).

J. Preparation of the Plasmid pBionR-FNR Antisense

Figure 2:
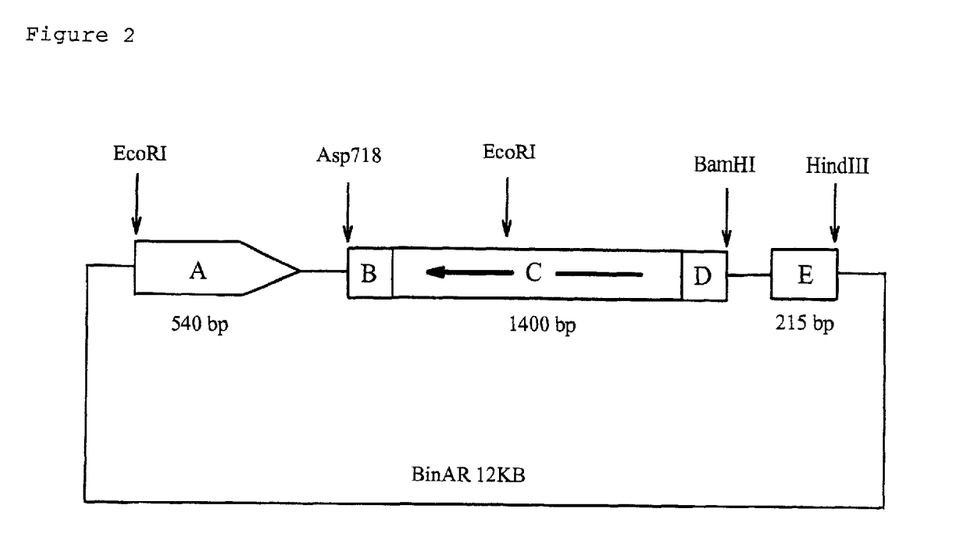
FIG. 2 shows a construction drawing of the chimeric gene which mediates the expression of NADP-dependent FNR antisense RNA.

The plasmid pBinAR-FNR-antisense is composed of the five fragments A, B, C, D and E (FIG. 2). The expression vector pBinAr contains fragment A, which carries the 35S CaMV promoter. This encompasses a fragment which encompasses nucleotides 6909 to 7437 of cauliflower mosaic virus (CaMV) (Franck et al. Cell 21 (1980), 285). It was isolated from plasmid pDH51 (Pietrzak et al. Nucleic. Acid Res. 14 (1986), 5857) as an EcoRI-KpnI fragment. Fragments B and D contain a subsequence of the multiple cloning site, and fragment C (FNR cDNA) was isolated from pBluescript SK as an Asp718-BamHI fragment, and the FNR cDNA was cloned into vector pBinAR as an Asp718-BamHI fragment in antisense orientation (FIG. 2). Fragment E contains the polyadenylation signal of gene 3 of the T-DNA of the Ti plasmid pTiACH5 (Gielen et al. EMBO J. 3 (1984), 835), nucleotides 11749–11939, which has been isolated from plasmid pAGV 40 (Herrera-Estrella et al. Nature 303 (1983), 209) as a PvuII-HindIII fragment and, after addition of SphI linkers to the PvuII cleavage site, had been cloned between the SphI-HindIII cleavage site of the vector. The resulting plasmid BinAR-FNR-antisense was transformed into tobacco with the aid of the agrobacterium system.

EXAMPLE 2

Plant Screening 80 plants were regenerated from each of the transformed tobacco plants and transferred into the greenhouse. FNR activity was detected both by directly measuring the enzyme activity after chloroplast purification and via western blot by means of immunochemical detection using the biotin/streptavidin system by Amersham-Buchler. In addition, expression of the antisense gene was checked with the aid of northern blot.

EXAMPLE 3

Measuring the FNR Enzyme Activity

The enzyme activity was measured on isolated chloroplasts by methods known from the literature (Meth. Enzymol. 69 (1980), 250–251).

Chloroplast isolation from leaves, fresh and dry weight determination and chlorophyll and protein content determination were carried out by standard methods.

EXAMPLE 4

Properties of the Antisense Plant FNR-44

|  | Wild type | FNR-44 |
| --- | --- | --- |
| Fresh weight leaves (g) | 11.3 +/− 1 | 3.2 +/− 0.4 |
| Dry weight leaves (g) | 0.9 +/− 0.1 | 0.2 +/− 0.03 |
| Fresh weight roots (g) | 2.7 +/− 0.4 | 0.47 +/− 0.1 |
| Dry weight roots (g) | 0.17 +/− 0.06 | 0.035 +/− 0.01 |
| mRNA (PSL/mm$^2$) | 118 +/− 6 | 15.5 +/− 4 |
| FNR activity (AU/min*mg) | 4.4 +/− 1.4 | 1.5 +/− 0.6 |

The plant FNR-44 exhibits a lower FNR mRNA content and a reduced enzyme activity. This results in reduced growth.

An enzyme inhibitor should therefore also inhibit the growth of plants.

EXAMPLE 5

Assay System for the Search for Ferredoxin:NADP Reductase Inhibitors

Ferredoxin:NADP reductase not only catalyzes the physiologically relevant, reversible reaction of NADP with ferrecoxin (ferredoxin reductase activity), but also the NADPH-dependent reduction of potassium hexacyanoferrate(III) (diaphorase activity). Methods for measuring these reactions are described in the literature (Meth. Enzymol., Volumes 23 and 69).

The diaphorase activity can be determined by incubating, for example, chloroplasts or isolated ferredoxin:NADP reductase (Sigma) in 100 mM Tris/HCl buffer, pH 8.2+0.5 mM potassium hexacyanoferrate(III)+0.5 mM NADPH or an NADPH-regenerating system such as, for example, 0.5 mM NADP+2.5 mM glucose-6-phosphate+1 unit/ml glucose-6-phosphate dehydrogenase at 25° C. and monitoring the decrease in absorption at 420 nm. An incubation mixture without ferredoxin:NADP reductase may be used as blank value.

The ferredoxin reductase activity can be determined by incubating, for example, chloroplast extracts or isolated ferredoxin:NADP reductase (Sigma) in 100 mM Tris/HCl buffer, pH 7.8+0.2 mM NADPH+0.65 mg/ml cytochrome C+0.1 mg/ml ferredoxin at 25° C. and measuring the change in the absorption at 550 nm, or the difference in absorption change at 550 nm and 540 nm. An incubation mixture without ferredoxin can be used as blank value.

The action of a test substance can be tested by dissolving the substance in a suitable solvent such as, for example, dimethyl sulfoxide and pipetting an aliquot of the solution to the above-described incubation mixture. A corresponding aliquot of the pure solvent may be used as control. The action of the test substance can be determined by comparing the absorption changes of the respective incubation batches.

EXAMPLE 6
Inhibition of Diaphorase Reaction:

EXAMPLE 7
Ferredoxin-NADP+ Oxidoreductase Inhibitors
Use Examples

The effect of the herbicidal compounds according to the invention on the growth of duckweed can be seen from the following test results: p The duckweed *Lemnna paucicostata* was grown under sterile conditions in 250 ml glass vessels containing 100 ml of inorganic nutrient solution supplemented with 1% sucrose, as described by Grossmann et al., Pesticide Science 35 (1992), 283–289. At the beginning of the test, 150 µl of a solution of active ingredient in acetone (stock solution: 100-fold concentrated) were pipetted into Petri dishes (diameter 6 cm, height 1.5 cm; Greiner, Frickenhausen) containing 15 ml of nutrient solution (without added sucrose). Only the solvent component of the active ingredient solution was added to the nutrient solution for the control tests. Then, 4 Lemna plants were introduced into each dish, the dishes were covered with lids and incubated in a controlled-environment cabinet at 25° C. under permanent light conditions (Phillips TL white neon tubes, approx. 40 µmol $m^{-2}s^{-1}$; λ=400–750 nm). After 8–10 days, the increase in leaf area was determined using an imaging apparatus (Imago, Compulog Computer Syst., Böblingen) as growth parameter, and this was used to calculate the % growth inhibition relative to the control.

The results of the tests can be seen from the table which follows. The herbicidal effect of the compounds according to the invention is demonstrated by a potent inhibition of the growth of Lemna.

|  | AU/min $*10^{-3}$ | % inhibition |
|---|---|---|
| Blank value[1] | 9.4 | 100 |
| Control (DMSO) | 31.3 | 0 |
| 50 µM compound I B.3 | 9.0 +/- 1.4 | 102 |

1 without ferredoxin:NADP reductase
2 mean +/- standard deviation of 6 experiments Inhibition of ferredoxin reductase reaction:

| Compound I according to the invention | Use concentration | Growth inhibition (% of the control) |
|---|---|---|
| A.28 | $10^{-4}$ M | 60 |
|  | $10^{-5}$ M | 42 |
|  | $10^{-6}$ M | 26 |
| A.46 | $10^{-4}$ M | 56 |
|  | $10^{-5}$ M | 33 |
|  | $10^{-6}$ M | 13 |
| A.47 | $10^{-4}$ M | 18 |

|  | E (550 –540) | % inhibition |
|---|---|---|
| Blank value[1] | 0.027 | 100 |
| Control (DMSO) | 0.692 | 0 |
| 1 mM compound I B.3 | 0.093 +/- 0.026 | 90 |

[1] without ferredoxin
[2] mean +/- standard deviation of 6 experiments

Compound 1 B.3

| Compound I according to the invention | Use concentration | Growth inhibition (% of the control) |
|---|---|---|
| A.48 | $10^{-4}$ M | 42 |
|  | $10^{-5}$ M | 34 |
|  | $10^{-6}$ M | 28 |
| A.49 | $10^{-4}$ M | 77 |
|  | $10^{-5}$ M | 49 |
|  | $10^{-6}$ M | 19 |
| A.51 | $10^{-4}$ M | 29 |
| A.52 | $10^{-4}$ M | 89 |
|  | $10^{-5}$ M | 12 |
| A.55 | $10^{-4}$ M | 28 |
| B.3 | $10^{-4}$ M | 96 |
|  | $10^{-5}$ M | 66 |
|  | $10^{-6}$ M | 54 |

EXAMPLE 8

Synthesis of 3-methyl-6-n-propylaminosulfonylbenzothiazolone-2-((2-n-butylsulfonyl)benzoic acid) hydrazone 0.33 g (0.0013 mol) of 2-(n-butylsulfonyl)benzohydrazide and 0.56 g (0.00126 mol) of 2-methylmercapto-3-methyl-6-(n-propylaminosulfonyl)benzimidazolium-p-toluene sulfate are refluxed for 6 hours in a mixture of 7 ml of pyridine and 7 ml of piperidine. The mixture is subsequently concentrated and the residue which remains is stirred with ethyl acetate. The insoluble residue is discarded, and the filtrate is concentrated and chromatographed on a silica gel column (methylene chloride/methanol 9:1).

Yield: 110 mg (m.p. 125–127° C.).

Similar: 3-methyl-6-sulfonylbenzothiazolone-2-((4-n-butylaminosulfonyl)benzoic acid) hydrazone (m.p. >250° C.).

EXAMPLE 9

Synthesis of 3-methyl-5-sulfonylbenzothiazolone-2((2-n-butyl-aminosulfonyl)benzoic acid) hydrazone

0.47 g (0.00172 mol) of 2-(n-butylaminosulfonyl)benzohydrazide and 0.75 g (0.00172 mol) of 2-methylmercapto-3-methyl-5-sulfonylbenzimidazolium p-toluene sulfate are refluxed for 6 hours in a mixture of 10 ml of pyridine and 10 ml of piperidine. The mixture is subsequently diluted with water and acidifed with hydrochloric acid. The resulting precipitate is filtered off with suction and dried.

Yield: 280 mg (m.p. 247° C., decomposition).

Similar: 3-methyl-5-sulfonylbenzothiazolone-2-((4-n-butylsulfonyl)benzoic acid) hydrazone (m.p. >250° C.)

We claim:

1. A method of using compounds of the formula I as herbicides or for the dessication/defoliation of plants, Formula I where =$\sim\!\sim$NH— represents the E/Z isomers, or a salt thereof in which Y: is C=O, $SO_2$ and the radicals R have the following meanings:

$R^1$, $R^2$, $R^3$: in each case independently of one another are hydrogen, halogen, cyano, $C_1$–$C_6$-alkyl, $C_1$–$C_6$-alkoxy, $C_1$–$C_6$-alkoxyalkyl, $C_1$–$C_6$-haloalkyl, $C_1$–$C_6$-alkylthio, $C_1$–$C_6$-haloalkoxy, $C_1$–$C_6$-alkylcarbonyl, $C_1$–$C_6$-alkoxycarbonyl, $S(O)_n$—$C_1$–$C_6$-alkyl, $S(O)_n$—$C_1$–$C_6$-haloalkyl, $S(O)_n$—N—$C_1$–$C_6$-alkyl, $S(O)_n$—N($C_1$–$C_6$-alkyl)$_2$ where n=0, 1, 2, $SO_3H$, COOH, $PO_3H$, $CONH_2$, CONH—$C_1$–$C_6$-alkyl, CO—N($C_1$–$C_6$-alkyl)$_2$, $NH_2$, NH—$C_1$–$C_6$-alkyl, N-($C_1$–$C_6$-alkyl)$_2$, hydrogen, $C_1$–$C_6$-alkyl, $R^5$, $R^6$, $R^7$: in each case independently of one another are hydrogen, halogen, cyano, $C_1$–$C_{30}$-alkyl, $C_1$–$C_{30}$-alkoxyalkyl, $C_1$–$C_{30}$-haloalkyl, $C_1$–$C_{30}$-alkylthio, $C_1$–$C_{30}$-haloalkoxy, $C_1$–$C_{30}$-alkylcarbonyl, $C_1$–$C_{30}$-alkoxycarbonyl, $SO_3H$, $S(O)_n$—$C_1$–$C_{30}$-alkyl, $S(O)_n$—$C_1$–$C_{30}$-haloalkyl, $S(O)_n$—N—$C_1$–$C_{30}$-alkyl, $S(O)_n$—N($C_1$–$C_{30}$-alkyl)$_2$ where n=0,1,2, COOH, $CONH_2$, CONH—$C_1$–$C_{30}$-alkyl, CO—N($C_1$–$C_{30}$-alkyl)$_2$, $NH_2$, NH—$C_1$–$C_{30}$-alkyl, N—($C_1$–$C_{30}$-alkyl)$_2$, by postemergence application to the plants or by preemergence application to the bare soil.

2. A composition suitable for controlling harmful plants by the process of claim 1 which comprises an effective amount of at least one compound of the formula I or of a salt thereof and at least one inert herbicidal formulation auxiliary.

3. A process for the preparation of the herbicidal composition of claim 2, wherein a herbicidally active amount of at least one compound of the formula I or a salt thereof is processed together with at least one inert herbicidal formulation auxiliary.

* * * * *